United States Patent [19]

Martin

[11] 4,093,739

[45] June 6, 1978

[54] MERCAPTOACYLAMIDOBENZOYL GLYCINE AND MUCOLYTIC PROCESS

[75] Inventor: Tellis Alexander Martin, Evansville, Ind.

[73] Assignee: Mead Johnson & Company, Evansville, Ind.

[21] Appl. No.: 806,877

[22] Filed: Jun. 15, 1977

[51] Int. Cl.² .................. A61K 31/205; C07C 149/00
[52] U.S. Cl. .............................. 424/316; 260/501.12; 260/516; 424/319
[58] Field of Search ............. 260/501.11, 501.12, 260/516; 424/316, 319

[56] References Cited

U.S. PATENT DOCUMENTS

| | | | |
|---|---|---|---|
| 2,520,293 | 8/1950 | Weiss | 260/516 |
| 3,091,569 | 5/1963 | Sheffner | 260/516 |
| 3,663,690 | 5/1972 | Eichel et al. | 424/319 |
| 3,809,697 | 5/1974 | Martin et al. | 260/268 C |
| 3,857,951 | 12/1974 | Buret | 424/319 |
| 3,950,387 | 4/1976 | Joullie et al. | 260/516 X |
| 3,971,828 | 7/1976 | Mita et al. | 424/319 |
| 4,005,222 | 1/1977 | Martin | 424/319 |
| 4,011,240 | 3/1977 | Mauvernay et al. | 260/516 X |

OTHER PUBLICATIONS

Sheffner, New York Acad. Sci., 106, 298–310, (1963).

*Primary Examiner*—James O. Thomas, Sr.
*Assistant Examiner*—G. T. Breitenstein
*Attorney, Agent, or Firm*—Robert H. Uloth; Robert E. Carnahan

[57] ABSTRACT

N-[3-(mercaptoacetylamino)benzoyl]glycine, alkali metal and amine salts thereof are potent topically effective mucolytic agents.

19 Claims, No Drawings

MERCAPTOACYLAMIDOBENZOYL GLYCINE AND MUCOLYTIC PROCESS

FIELD OF THE INVENTION

This invention is concerned with carbon compounds having drug and bio-affecting properties. In particular, the invention relates to N-[3-(mercaptoacetylamino)-benzoyl]glycine and salts thereof. These compounds are mucolytic agents and another aspect of the invention involves their use in a process for effecting mucolysis of pulmonary secretions.

DESCRIPTION OF THE PRIOR ART

Sheffner, U.S. Pat. No. 3,091,569, relates to N-acylated sulfhydryl compounds such as N-acetyl-L-cysteine which is a known pharmaceutical therapeutically used as a topically administered mucolytic agent under the trademark Mucomyst.

Martin, et al., U.S. Pat. No. 3,809,697, describes a group of 1,4-bis-(mercaptoacetyl)piperazines having mucolytic properties.

Martin, et al., U.S. Pat. No. 4,005,222, teaches that certain mercaptoacylamidobenzoic acids such as 3-(2-mercaptoacetamido)benzoic acid disclosed in Weiss, U.S. Pat. No. 2,520,293 are mucolytic agents.

A. L. Sheffner, Ann. New York Acad. Sci. 106, 198-310 (1963) discloses that a variety of sulfhydryl containing compounds such as N-acetyl-L-cysteine have mucolytic activity and, in an attempt to correlate mucolytic activity and chemical structure, stated that compounds having a free sulfhydryl group were generally effective in reducing mucus viscosity.

One problem associated with the use of sulfhydryl compounds in the field of mucolytic agents is the inherent ease with which they are oxidized to form mucolytically inactive disulfides, e.g., $2\ RSH \rightarrow R{-}S{-}S{-}R$. This sensitivity to oxygen requires special handling and packaging, e.g., under nitrogen to maintain potency and maximize shelf life. The principle object of the present invention is the provision of improved sulfhydryl containing mucolytic agents which are both potent and relatively stable to disulfide formation. Another object is to provide a sulfhydryl containing mucolytic agent which is in flowable powder form for direct delivery to the airway including the lungs by inhalation. For this purpose, crystalline salts are preferred which remain relatively unchanged when exposed to normal room temperature and humidity conditions. Further and additional objects will appear from the following description and accompanying claims.

SUMMARY OF THE INVENTION

Broadly described, this invention is concerned with N-[3-(mercaptoacetylamino)benzoyl]glycine and pharmaceutically acceptable salts thereof. These substances have utility as mucolytic agents and a further embodiment of the invention relates to a process for liquifying mucus by contacting an effective mucolytic amount of N-[3-(mercaptoacetylamino)benzoyl]glycine or salt thereof with the mucus.

DETAILED DESCRIPTION OF THE INVENTION

The instant invention, as indicated hereinabove, is concerned with a sulhydryl compound selected from the group consisting of N-[3-(mercaptoacetylamino)-benzoyl]glycine characterized by formula I

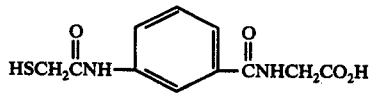

and a pharmaceutically acceptable salt thereof wherein said salt is anhydrous or hydrated.

As used herein, the term "pharmaceutically acceptable" is descriptive of salts whose cationic species do not contribute appreciably to the toxicity of the product nor its pharmacological activity. Such salts considered within the scope of the present invention are the salts of alkali metals, e.g., sodium, potassium, calcium, barium, and the like as well as those prepared from ammonia and organic bases such as primary, secondary, and tertiary aliphatic amines. A preferred group of salts are those prepared from ammonia, trimethylamine, triethylamine, ethanolamine, methylethanolamine, diethanolamine, triethanolamine, ethylenediamine.

The process for preparing the compound of formula I is carried out from 3-(chloroacetylamino)benzoic acid according to the following reaction sequence.

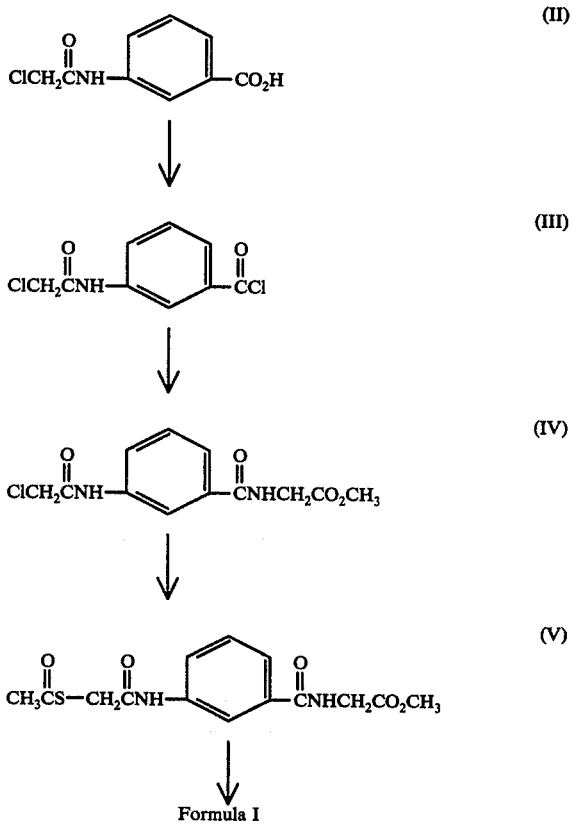

In the foregoing procedure, the acid chloride (III) is readily obtained in yields of 77-96% by reacting thionyl chloride and 3-(chloroacetylamino)benzoic acid (II) preferably in the presence of a trace of pyridine in a reaction inert solvent such as chloroform or ethylene dichloride. Reaction of the acid chloride (III) with glycine methyl ester in the presence of a base such as sodium bicarbonate provides the glycyl amide (IV) which is further reacted with an alkali metal salt (e.g., sodium or potassium) of thiolacetic acid in a solvent such as methanol to provide the thioester (V). Hydrolysis of the thioester (V) employing an alkoxide such as sodium or potassium methoxide or a base such as sodium hydroxide or potassium hydroxide in a reaction inert solvent such as methanol, ethanol, dimethylformamide and the like followed by acidification provides the formula I product as the free acid. The hydrolysis is preferably carried out under nitrogen in order to exclude oxidation of the free sulfhydryl to the disulfide.

The compound of formula I may be partially or completely neutralized to form salts by adjusting the pH with appropriate amounts of alkaline reacting substances such as sodium hydroxide, potassium hydroxide, ammonium hydroxide, calcium hydroxide, ammonia, ethanolamine, diethanolamine, triethanolamine, ethylenediamine, and the like, in a suitable solvent. Such salts are considered biologically equivalent to the parent acid with respect to mucolytic activity. The conversion of the formula I acid to the salt is carried out generally by adding an equivalent of the base to a mixture of the acid in tetrahydrofuran employing a trace of a sequestering agent such as disodium edetate, i.e. (ethylenedinitrilo)-tetraacetic acid disodium salt. Recovery of the salt obtained by neutralization of the formula I acid is carried out by conventional techniques such as evaporation, lyophylization, or precipitation. Some of the salts obtained in this manner are hydrated while others are anhydrous. For instance, the sodium salt of N-[3-(mercaptoacetylamino)benzoyl]glycine is obtained as a hydrate having from 1 to 3.5 moles of water per mole of salt by neutralization of the acid with 10% sodium hydroxide. Sodium salt hydrates containing less than 3.5 mole of water per mole of acid are metastable and take up additional moisture under atmospheric conditions to provide the sodium salt as a relatively stable 3.5 hydrate. The ammonium and potassium salts of N-[3-(mercaptoacetylamino)benzoyl]glycine also exemplify salts which form hydrates. As previously stated, not all salts form hydrates, for instance, two molecular equivalents of N-[3-(mercaptoacetylamino)benzoyl]glycine combine with 1 molecular equivalent of ethylenediamine to form a non-hygroscopic anhydrous salt.

The mucolytic activity of N-[3-(mercaptoacetylamino)-benzoyl]glycine and salts thereof can be determined according to standard in vitro mucolytic assays such as that described by J. Lieberman, Am. J. Resp. Dis. 97, 662 (1968). The Lieberman method consists of a viscometric procedure employing a cone-plate viscometer (Brookfield Engineering Laboratories, Inc., Stoughton, Mass.). To assay for mucolytic activity, a 2 ml. aliquot of a batch of pooled purulent human sputum (obtained from chronic bronchitis and asthmatic patients) is transferred to the center of a viscometer plate and the temperature is allowed to equilibrate. The plate is then rotated at gradually increasing speeds up to 100 r.p.m. during a 2-minute period. This reduces the amount of sputum on the test plate to 1 ml. and reduces the viscosity of the specimen to a reproducable value which is necessary because of the thixotropic properties of sputum. The rotation is reduced to give a convenient reading on the instrument and a solution of the test drug having a volume of 0.2 ml. is then added to the sputum cup and readings as percent reduction in viscosity of the original are recorded at timed intervals for a total period of 15 min. Repeating the test with a standard mucolytic agent such as N-acetyl-L-cysteine establishes a control value from which relative molar potencies of the test agent compared to control can be determined.

In the foregoing test, N-[3-(mercaptoacetylamino)-benzoyl]-glycine free acid and salts thereof such as the sodium salt, ethylenediamine salt, etc. were shown to be 8 to 14 times more active than N-acetyl-L-cysteine on a molar basis.

It will be recognized by those skilled in the art that the mucolytic process of the present invention may be practiced in vivo as well as in vitro. The in vivo process is employed where it is desirable or necessary to liquify mucus produced as a result of pathological conditions involving mucus producing tissue, particularly for example, congestion of the respiratory system, vaginal tract and the like. The in vitro process is employed where it is desirable to reduce viscosity of mucus in order to facilitate analytical determination or other examination. For instance, the compound of Formula I can be used as sputum digestant in the isolation of mycobacteria. The concentration in which the compound of Formula I has been found to effectively induce liquefaction of mucus is between about 0.003 to 0.5 molar. In carrying out the in vitro mucolytic process of the present invention, an aqueous solution or suspension of the formula I compound in an appropriate vehicle is prepared at the desired concentration and then mixed with mucus at a ratio of about 0.2 ml. to each 1.0 ml. of mucus. This concentration provides satisfactory liquefaction of the mucus within a period of about 1 to 15 minutes. It is to be understood that in addition to pharmaceutically acceptable salts of the formula I compound, other suitable cationic species can be employed in the in vitro process which would be generally precluded in the in vivo process because of excessive toxicity.

In accordance with the in vivo process of the present invention, the formula I compound and pharmaceutically acceptable salts thereof are administered in an amount sufficient to induce liquefaction of mucus in the respiratory tract of mammals in need thereof. Intratracheal administration of the formula I compound is effected by various inhalation or insufflation means such as by nose drops, sprays, aerosols, insufflation and the like. Solutions of sodium or ethylenediamine salts are relatively stable to disulfide formation and, accordingly, are particularly preferred. Solutions or suspensions having about 0.5 to 5% by weight of the formula I compound are stable for application by spraying with an atomizer, nebulizer, aerosol and the like. Another suitable and preferred method of administration is by means of an insufflator. For this purpose, N-[3-(mercaptoacetylamino)benzoyl]-glycine and pharmaceutically acceptable salts thereof must be micronized, e.g., to particles in the 1–4 micron range, or ground to ultrafine powder.

It will be readily apparent to those skilled in the medical arts, that the correct dosage of a compound of formula I to be employed with any particular mammalian subject is determined by the severity of the condition requiring mucolytic therapy, as well as the age, weight, and general physical condition of the subject. Individual doses ranging from 5–100 mg. for inhalation by man are suitable and may be repeated as required for the desired mucolytic effect.

A preferred insufflator for administering the formula I compound and salts thereof is described in U.S. Pat. No. 3,518,992 (incorporated herein by reference). This mechanical device which utilizes only the inspiratory energy of the inhaler requires a sealed two-piece hard gelatin capsule containing a single unit dose of the medicament with or without an excipient such as lactose. Thus, in order to be of routine value for use in the oral inhaler of U.S. Pat. No. 3,518,992, the active ingredient of the instant invention must be a solid capable of being finely powdered or preferably micronized. In addition, the active ingredient must be stable to normal atmospheric conditions and relatively non-hygroscopic in order to insure uniform deliverability.

To determine whether N-[3-(mercaptoacetylamino)-benzoyl]-glycine or a particular salt thereof is stable to normal atmospheric conditions, i.e., does not degrade to the disulfide, powdered samples are sealed in ampules with air or oxygen in the head space and then stored in the dark at room temperature (RT) (24°–27° C.), 40° C., and 50° C. Ampules are withdrawn from storage at intervals and the contents analyzed by high performance liquid chromatography (HPLC). Results for sodium, ammonium, and ethanolamine salts are given below in tables I–III.

TABLE I

Powder Stability of Micronized Sodium Salt of N-[3-Mercaptoacetylamino)benzoyl]glycine 3.5 Hydrate

| Storage Conditions | | % Disulfide$^a$ | | | | | |
|---|---|---|---|---|---|---|---|
| Temp. | Head Space | | | | | | |
| RT | | 6 Days | 8 Days | 15 Days | 26 Days | 35 Days | |
| | Air | 7.6 | 7.4 | 7.7 | 7.3 | 7.7 | — |
| | O$_2$ | 7.4 | 7.2 | 7.3 | 7.1 | 7.2 | — |
| 40° | | 4 Days | 7 Days | 14 Days | 27 Days | — | 41 Days |
| | Air | 7.2 | 8.1 | 7.8 | 8.8 | — | 9.0 |
| | O$_2$ | 8.9 | 8.8 | 9.2 | 10.0 | — | 10.4 |
| 50° | | — | 7 Days | 16 Days | 28 Days | — | — |
| | Air | — | 9.9 | 14.9 | 23.5 | — | — |
| | O$_2$ | — | 15.4 | 34.2 | — | — | — |

$^a$At zero days the disulfide content was 6.5%.

TABLE II

Powder Stability of Micronized Ammonium Salt of N-[3-(Mercaptoacetylamino)benzoyl]glycine Sesquihydrate

| Storage Conditions | | % Disulfide | | | | |
|---|---|---|---|---|---|---|
| Temp. | Head Space | 0 Days | 7 Days | 14 Days | 34 Days | 42 Days |
| RT | Air | 3.7 | 3.8 | 3.4 | 4.7 | 3.9 |
| | O$_2$ | 3.7 | 3.7 | 4.2 | 4.1 | 3.8 |
| 40° | Air | 3.7 | 4.8 | 6.0 | 9.7 | 10.1 |
| | O$_2$ | 3.7 | 5.4 | 9.0 | 29.4 | 67.4 |
| 50° | Air | 3.7 | 10.3 | 14.8 | 26.2 | 27.6 |
| | O$_2$ | 3.7 | 16.5 | 21.7 | 31.0 | 45.0 |

TABLE III

Powder Stability of the Ethanolamine Salt of N-[3-(Mercaptoacetylamino)benzoyl]glycine

| Storage Conditions | | % Disulfide | | | | | |
|---|---|---|---|---|---|---|---|
| Temp. | Head Space | 0 Days | 8 Days | 15 Days | 27 Days | 42 Days | 56 Days |
| RT | Air | 3.4 | 4.0 | 3.2 | 3.5 | 3.6 | — |
| | O$_2$ | 3.4 | 3.2 | 3.2 | 3.3 | 3.5 | 3.5 |
| 40° | Air | 3.4 | 3.7 | 3.8 | 4.4 | 5.3 | — |
| | O$_2$ | 3.4 | 3.5 | 3.7 | 4.1 | 3.8 | 4.5 |
| 50° | Air | 3.4 | 4.6 | 4.8 | 7.6 | 11.1 | 14.0 |
| | O$_2$ | 3.4 | 3.9 | 4.4 | 10.7 | 14.4 | 26.2 |

The data summarized in Tables I–III above shows that all of the salts are relatively stable at room temperature under air or oxygen. At 40° C. both the sodium and ethanolamine salts are substantially more stable than the ammonium salt (which shows a relative instability after 14 days of storage) and are, accordingly, preferred with respect to sulfhydryl stability.

As previously stated, in order for a medicament to be useful for routine administration by insufflation, the medicament must be relatively non-hygroscopic. Table IV indicates the degree of hygroscopicity of various salts of N-[3-(mercaptoacetylamino)benzoyl]glycine.

TABLE IV

Hygroscopicity of N-[3-(Mercaptoacetylamino)-benzoyl]glycine Salts at 58% Relative Humidity

| Salt | Initial Moles of H$_2$O of Hydration | Days | Moisture Gain, % | Hygroscopicity |
|---|---|---|---|---|
| Sodium | 1.5 | 6 | 9.0 | Yes |
| Sodium | 3.5 | 10 | −0.05 | No |
| Potassium | 1 | 10 | 2.1 | Yes |
| Ammonia | 1.5 | 10 | −0.28 | No |
| Ethanolamine | 0 | 12 | 2.1 | Yes |
| Diethanolamine | 0 | 11 | 7.7 | Yes |

It is evident from the above data that the sodium 3.5 hydrate salt is relatively non-hygroscopic and, accordingly, is a preferred salt form of N-[3-(mercaptoacetylamino)benzoyl]glycine for administration by insufflation.

The compound of formula I is a relatively non-toxic substance substantially free of other pharmacological action. Thus, N-[3-(mercaptoacetylamino)benzoyl]glycine has an approximate oral TD$_{50}$ and LD$_{50}$ of more than 2,000 mg/kg body weight in the mouse.

The following examples are only intended to illustrate the present invention and are not to be construed as limiting the invention in any respect.

EXAMPLE 1

N-[3-(Mercaptoacetylamino)benzoyl]glycine (a) 3-(Chloroacetylamino)benzoyl Chloride.

To a warm (55°–60° C.) solution of 250 ml. of thionyl chloride and 50 ml. of chloroform and 6 drops of pyridine is added 3-(chloroacetylamino)benzoic acid (150 g., 0.702 mole) in 3 equal portions at 0.5 hr. intervals. After the addition is complete, the reaction mixture is warmed to a temperature of 55°–65° C. for 2 hrs., cooled and diluted with 500 ml. of petroleum ether (b.p. 30°–60° C.). The precipitate which forms is collected, washed with petroleum ether (b.p. 30°–60° C.) and dried under vacuum over potassium hydroxide at room temperature to afford 143 g. (80% yield) of 3-(chloroacetylamino)benzoyl chloride, m.p. 106°–108° C.

(b) N-[3-(Chloroacetylamino)benzoyl]glycine methyl ester.

To a mixture of glycine methyl ester hydrochloride (358 g., 2.85 mole) and 2.4 l. of water is added sodium bicarbonate (239.4 g., 2.85 mole). After stirring at room temperature for 0.5 hr., the mixture is diluted with 1 l. of methanol, cooled at 0° C. while sodium bicarbonate (239.4 g., 2.85 mole) is added followed by portionwise addition of 3-(chloroacetylamino)benzoylchloride (650 g., 2.8 mole) during a 0.75 hr. period. Considerable foaming takes place when approximately one-half of the acid chloride has been added and is controlled by periodic addition of small quantities of methanol. The reaction mixture is stirred for 16 hrs., diluted with 800 ml. of water and then stirred for an additional 0.5 hr. to provide a solid which is collected and sequentially washed with 500 ml. of 50% methanol, 2 l. of water, and 500 ml. of 50% methanol. The washed material is first air dried for 3 days and then for 12 hrs. under reduced pressure at 45° C. to afford 626.7 g. (77% yield) of N-[3-(chloroacetylamino)benzoyl]glycine methyl ester, m.p. 122.0°–124.0° C. Analytically pure N-[3-(chloroacetylamino)benzoyl]glycine methyl ester is obtained by crystallization from methanol, m.p. 122°–127° C.

Anal. Calcd. for $C_{12}H_{13}ClN_2O_4$ (%): C, 50.63; H, 4.60; N, 9.84. Found (%): C, 50.78; H, 4.57; N, 9.71.

(c) N-[3-(Acetylthioacetylamino)benzoyl]glycine methyl ester.

A solution of potassium thiolacetate is prepared by adding 495 ml. of 2N-methanolic potassium hydroxide (0.99 mole) during a period of 15 min. to a solution of 74.3 ml. of thiolacetic acid (79.1 g., 1.04 mole) and 500 ml. of methanol while maintaining a temperature of 1°–5° C. The methanolic potassium thiolacetate solution thus prepared is added over 0.5 hr. to a mixture of N-[3-(chloroacetylamino)benzoyl]glycine methyl ester (267.5 g., 0.94 mole) in 2 l. of methanol while maintaining a temperature of 0°–5° C. After stirring for a period of 1 hr. without cooling, the reaction mixture is warmed at 40°–45° C. for 2 hrs., cooled, and filtered. The material collected is sequentially washed with 50% methanol, water, and 50% methanol, and then air dried to afford 262.4 g. (86% yield) of N-[3-(acetylthioacetylamino)benzoyl]glycine methyl ester, m.p. 86°–88° C. Crystallization from methanol provides analytically pure N-[3-(acetylthioacetylamino)benzoyl]glycine methyl ester, m.p. 90.0°–92.0° C.

Anal. Calcd. for $C_{14}H_{16}N_2O_5S$ (%): C, 51.84; H, 4.97; N, 8.64. Found (%): C, 51.95; H, 5.01; N, 8.62.

(d) N-[3-(Mercaptoacetylamino)benzoyl]glycine.

An aqueous 10% sodium hydroxide solution (12 ml., 0.03 mole) is added to a slurry of N-[3-(acetylthioacetylamino)benzoyl]glycine methyl ester (2.8 g., 0.0086 mole) in 30 ml. of methanol under a nitrogen atmosphere. The resulting solution is stirred at 25° C. for 1 hr., cooled, acidified with 5.3 ml. of 6 N hydrochloric acid and filtered. The material collected is sequentially washed with 50% methanol, water and 50% methanol to provide 2.4 g. (90%) of analytically pure N-[3-(mercaptoacetylamino)benzoyl]glycine, m.p. 207.0°–209.0° C. (dec.).

Anal. Calcd. for $C_{11}H_{12}N_2O_4S$ (%): C, 49.24; H, 4.51; N, 10.44; SH, 12.33. Found (%): C, 49.14; H, 4.48; N, 10.36; SH, 12.32.

EXAMPLE 2

(a) N-[3-(Mercaptoacetylamino)benzoyl]glycine Ammonium salt.

To N-[3-(mercaptoacetylamino)benzoyl]glycine (.0.8 g., 0.003 mole) in 8 ml. of methanol is added dropwise 1.1 ml. of 3N ammonium hydroxide under nitrogen. The nitrogen atmosphere is maintained and excess solvent removed by warming the resulting solution to 40°–45° C. After stirring residue overnight with isopropanol under nitrogen, the mixture is filtered and the material collected, washed with acetone, and dried in a vacuum dessicator over potassium hydroxide to provide 0.75 g. (88% yield) of analytically pure N-[3-(mercaptoacetylamino)benzoyl]glycine ammonium salt, m.p. 144.0°–154.0° C. (dec.).

Anal. Calcd. for $C_{11}H_{11}N_2O_4S \cdot NH_4$ (%): C, 46.31; H, 5.30; N, 14.73; SH, 11.59. Found (%): C, 46.24; H, 5.31; N, 14.52; SH, 12.17.

(b) N-[3-(Mercaptoacetylamino)benzoyl]glycine Ammonium Salt Sesquihydrate.

An aqueous solution of 3N ammonium hydroxide (7.2 ml., 0.0216 mole) is slowly added to a suspension of N-[3-(mercaptoacetylamino)benzoyl]glycine (5 g., 0.0186 mole) in 40 ml. of tetrahydrofuran with 5 mg. of disodium edetate. The resulting solution is diluted with 300 ml. of tetrahydrofuran and after cooling in a dry ice-ethanol bath to promote crystallization is stirred overnight. The precipitated solid is collected, washed with tetrahydrofuran and air dried to afford 4.6 g., (79.3% yield) of N-[3-(mercaptoacetylamino)benzoyl]glycine ammonium salt susquihydrate, m.p. 56°–119° C. (dec.).

Anal. Calcd. for $C_{11}H_{11}N_2O_4S \cdot NH_4 \cdot 1.5H_2O$ (%): C, 42.30; H, 5.81; N, 13.45; SH, 10.59. Found (%): C, 42.40; H, 5.53; N, 13.23; SH, 10.37.

EXAMPLE 3

(a) N-[3-(Mercaptoacetylamino)benzoyl]glycine Sodium Salt Sesquihydrate.

An aqueous solution of 1.5 ml. of 10% sodium hydroxide is slowly added to a mixture of N-[3-(mercaptoacetylamino)-benzoyl]glycine (1 g., 0.00373 mole) and 1 mg. of disodium edetate in 20 ml. of tetrahydrofuran with cooling. After standing 0.5 hr., the mixture is filtered and the material collected washed with tetrahydrofuran and dried for 16 hr. under vacuum over calcium chloride to provide 1.1 g. (93% yield) of N-[3-(mercaptoacetylamino)benzoyl]glycine sodium salt sesquihydrate, m.p. 74°–124° C. (dec.).

Anal. Calcd. for $C_{11}H_{11}N_2O_4S \cdot Na \cdot 1.5H_2O$ (%): C, 41.64; H, 4.45; N, 8.83; SH 10.42. Found (%): C, 41.34; H, 4.18; N, 8.82; SH, 10.19.

(b) N-[3-(Mercaptoacetylamino)benzoyl]glycine Sodium Salt Dihydrate.

An aqueous solution of 10% sodium hydroxide (7.5 ml., 0.01875 mole) is slowly added to a mixture of N-[3-(mercaptoacetylamino)benzoyl]glycine (5 g., 0.0186 mole) and 5 mg. of disodium edetate in 60 ml. of tetrahydrofuran with cooling at ice water temperature. The mixture stirred and equilibrated to room temperature first provides a complete solution and subsequently a solid precipitate which is stirred for an additional 0.5 hr. and filtered. The collected solid is washed with three 20 ml. portions of tetrahydrofuran and then dried under vacuum over calcium chloride to provide 4 g. (66% yield) of N-[3-(mercaptoacetylamino)benzoyl]-glycine sodium salt dihydrate, m.p. 108°–136.0° C. (dec.).

Anal. Calcd. for $C_{11}H_{11}N_2O_4S \cdot Na \cdot 2H_2O$ (%): C, 40.49; H, 4.63; N, 8.59; SH, 10.14. Found (%): C, 40.80; H, 4.32; N, 8.48; SH, 10.14.

(c) N-[3-(Mercaptoacetylamino)benzoyl]glycine Sodium Salt Monohydrate.

The dihydrate obtained above in Example 3(b) dried at 60° C. under vacuum for 0.5 hr. provided the monohydrate of N-[3-(mercaptoacetylamino)benzoyl]glycine sodium salt, m.p. 117°–165° C. (dec.).

Anal. Calcd. for $C_{11}H_{11}N_2O_4S \cdot Na \cdot H_2O$ (%): C, 42.86; H, 4.25; N, 9.09; SH, 10.73. Found (%): C, 42.77; H, 4.43; N, 8.91; SH, 10.67.

(d) Stable Hydrate of N-[3-(mercaptoacetylamino)benzoyl]glycine Sodium Salt.

An aqueous solution of 10% sodium hydroxide (65 ml., 0.1625 mole) is slowly added to a suspension of N-[3-(mercaptoacetylamino)benzoyl]glycine (43 g., 0.16 mole) in 230 ml. of tetrahydrofuran with cooling at 10°-20° C. The mixture is warmed to about 20°-25° C. and filtered from a trace of solid. Diluting the filtrate with 480 ml. of tetrahydrofuran promotes the formation of a suspension which is stirred for 2 hr. and collected. The collected material is washed with tetrahydrofuran and air dried to provide 50 g. (88.3% yield) of N-[3-(mercaptoacetylamino)benzoyl]glycine sodium salt hydrated with 3.5 moles water, m.p. 68°-120° C. (dec.).

Anal. Calcd. for $C_{11}H_{11}N_2O_4S \cdot Na \cdot 3.5\ H_2O$ (%): C, 37.39; H, 5.13; N, 7.93; SH, 9.36; $H_2O$, 17.8. Found (%): C, 37.65; H, 5.07; N, 7.70; SH, 9.04.

Exposure of the monohydrate of Example 3(c) to air for a period of 3 days provides the stable hydrate form of N-[3-(mercaptoacetylamino)benzoyl]glycine sodium salt, m.p. 66°-120° C. (dec.).

Anal. Found (%): C, 37.43; H, 4.88; N, 7.84; SH, 9.37; $H_2O$, 17.22.

EXAMPLE 4

N-[3-(Mercaptoacetylamino)benzoyl]-glycine Potassium Salt Hydrate

An aqueous solution of 4N potassium hydroxide (4.65 ml., 0.01 mole) and 4 ml. of water is slowly added to a suspension of N-[3-(mercaptoacetylamino)benzoyl]glycine (5 g., 0.0186 mole) with 5 mg. disodium edetate. Warming the mixture to 45° C. provides a clear solution which is first diluted with 200 ml. of tetrahydrofuran and then cooled in a dry ice-ethanol bath to promote crystallization. After stirring the mixture for a period of 16 hr. at 25° C., the precipitated solid is collected, washed with tetrahydrofuran and dried under vacuum over calcium chloride to provide 5.6 g. (93% yield) of N-[3-(mercaptoacetylamino)benzoyl]glycine potassium salt hydrate, m.p. 175° C. (dec.).

Anal. Calcd. for $C_{11}H_{11}N_2O_4S \cdot K \cdot H_2O$ (%): C, 40.73; H, 4.04; N, 8.64; SH, 10.19. Found (%): C, 40.51; H, 3.88; N, 8.38; SH, 9.77.

EXAMPLE 5

N-[3-(Mercaptoacetylamino)benzoyl]glycine 2-Hydroxyethyl Ammonium Salt

A solution 1.13 ml. of ethanolamine (1.15 g., 0.0188 mole) and 10 ml. of tetrahydrofuran is added to a suspension of N-[3-(mercaptoacetylamino)benzoyl]glycine (5 g., 0.0186 mole), 5 mg. of disodium edetate, 6 ml. of water, and 40 ml. of tetrahydrofuran. Warming the mixture to 40°-45° C. provides a clear solution which is first diluted with 200 ml. of tetrahydrofuran, then cooled in a dry ice-acetone bath to promote crystallization and subsequently stirring for a period of 16 hrs. at room temperature. The precipitated material formed is collected, washed with tetrahydrofuran and dried over calcium chloride to afford 5.7 g., (93% yield) of N-[3-(mercaptoacetylamino)benzoyl]glycine 2-hydroxyethyl ammonium salt, m.p. 144.0°-160.0° C. (dec.).

Anal. Calcd. for $C_{11}H_{11}N_2O_4S \cdot C_2H_8NO$ (%): C, 47.41; H, 5.82; N, 12.76; SH, 10.04. Found (%): C, 47.19; H, 5.76; N, 12.72; SH, 9.86.

EXAMPLE 6

N-[3-(Mercaptoacetylamino)benzoyl]glycine-bis-(2-hydroxyethyl) Ammonium Salt

A solution of 1.82 ml. diethanolamine (2 g., 0.0189 mole) in 10 ml. of tetrahydrofuran is added to a mixture of N-[3-(mercaptoacetylamino)benzoyl]glycine (5 g., 0.0186 mole), 5 mg. of disodium edetate, 4 ml. of water and 40 ml. of tetrahydrofuran under an atmosphere of nitrogen during a 5-minute period at room temperature. The resulting mixture is first warmed to 40°-45° C. for 20 min. and then cooled in a dry ice-ethanol bath for 0.5 hr. to promote crystallization. Cooling is discontinued and the mixture stirred overnight under an atmosphere of nitrogen and filtered. The material collected is washed with tetrahydrofuran and then dried under vacuum over calcium chloride to provide 5.8 g., of the bis-(2-hydroxyethyl) ammonium salt of N-[3-(mercaptoacetylamino)benzoyl]glycine, m.p. 64°-74.5° C. (dec.).

Anal. Calcd. for $C_{11}H_{11}N_2O_4S \cdot C_4H_{12}NO_2$ (%): C, 48.25; H, 6.21; N, 11.25; SH, 8.86. Found (%): C, 48.24; H, 6.35; N, 11.22; SH, 8.43.

EXAMPLE 7

N-[3-(Mercaptoacetylamino)benzoyl]glycine 1,2-ethanediammonium Salt

A solution of 0.62 ml. of ethylenediamine (0.56 g., 0.0093 mole) in 10 ml. of tetrahydrofuran is added during a 10-min. period to a mixture of N-[3-(mercaptoacetylamino)benzoyl]glycine (5 g., 0.0186 mole), 5 mg. of disodium edetate, 6 ml. of water and 40 ml. of tetrahydrofuran under an atmosphere of nitrogen. The resulting solution is stirred at 25° C. for 0.5 hr. and then diluted with 200 ml. of tetrahydrofuran. After stirring for a period of 16 hr. at room temperature under an nitrogen atmosphere, the white solid which formed is collected, washed with tetrahydrofuran and dried under vacuum over calcium sulfate to provide 3.9 g., of 1,2-ethanediammonium salt of N-[3-(mercaptoacetylamino)benzoyl]glycine, m.p. 204.5°-205.5° C. (dec.).

Anal. calcd. for $(C_{11}H_{11}N_2O_4S)_2 \cdot C_2H_{10}N_2$ (%): C, 48.31. H, 5.41; N, 14.08; SH, 11.08. Found (%): C, 48.01; H, 5.31; N, 13.82; SH, 10.58.

EXAMPLE 8

Powder for Administration Via Inhaler Device

| Ingredient | Amount |
|---|---|
| N-[3-(mercaptoacetylamino)benzoyl]-glycine sodium salt 3.5 hydrate micronized | 20 g. |
| Lactose powder | 20 g. |

The powders are blended aseptically and filled into hard gelatin capsules each containing 40 mg. of the mixture. This is suitable for dispersion into the inspired breath by means of a breath-operated inhaler device containing means for rupture of the capsule wall prior to dosing.

What is claimed is:

1. A compound selected from the group consisting of N-[3-(mercaptoacetylamino)benzoyl]glycine characterized by formula I

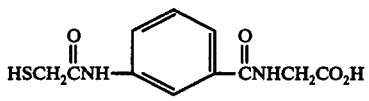

and a pharmaceutically acceptable salt thereof.

2. The salt claimed in claim 1 in stable crystalline form.

3. The compound according to claim 2 which is N-[3-(mercaptoacetylamino)benzoyl]glycine sodium salt.

4. The compound according to claim 2 which is N-[3-(mercaptoacetylamino)benzoyl]glycine sodium salt 3.5 hydrate.

5. The compound according to claim 2 which is N-[3-(mercaptoacetylamino)benzoyl]glycine 1,2-ethanediammonium salt.

6. The compound according to claim 2 which is N-[3-(mercaptoacetylamino)benzoyl]glycine potassium salt.

7. The compound according to claim 2 which is N-[3-(mercaptoacetylamino)benzoyl]glycine potassium salt monohydrate.

8. The compound according to claim 2 which is N-[3-(mercaptoacetylamino)benzoyl]glycine bis-(2-hydroxyethyl)ammonium salt.

9. The compound according to claim 2 which is N-[3-(mercaptoacetylamino)benzoyl]glycine ammonium salt sesquihydrate.

10. The compound according to claim 2 which is N-[3-(mercaptoacetylamino)benzoyl]glycine 2-aminoethane salt.

11. The compound according to claim 2 which is N-[3-(mercaptoacetylamino)benzoyl]glycine.

12. A process for liquefaction of mucus which comprises contacting said mucus with a mucolytic effective amount of a compound selected from the group consisting of N-[3-(mercaptoacetylamino)benzoyl]glycine characterized by Formula I

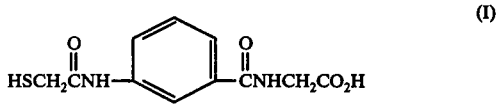

and a pharmaceutically acceptable salt thereof.

13. The process as claimed in claim 12 wherein said contacting step is carried out within the respiratory tract of a mammal.

14. The process as claimed in claim 12 wherein said contacting step is carried out in vitro.

15. The process as claimed in claim 12 wherein said mucus is contacted with about 0.003 to 0.5 molar solution of said compound for a time sufficient to liquify said mucus.

16. The process as claimed in claim 15 wherein said time is from 1 to 15 minutes.

17. The process as claimed in claim 12 wherein said compound is N-[3-(mercaptoacetylamino)benzoyl]glycine sodium salt 3.5 hydrate.

18. The process as claimed in claim 12 wherein said compound is N[3-(mercaptoacetylamino)benzoyl]glycine sodium salt.

19. The process as claimed in claim 12 wherein said compound is N-[3-(mercaptoacetylamino)benzoyl]glycine 1,2-ethanediammonium salt.

* * * * *